United States Patent [19]

Jelich et al.

[11] Patent Number: 4,854,964

[45] Date of Patent: Aug. 8, 1989

[54] TRIAZOLO-PYRIMIDINE-2-SULPHONA-MIDES HAVING HERBICIDAL UTILITY

[75] Inventors: Klaus Jelich, Wuppertal; Hans-Joachim Santel, Leverkusen; Robert R. Schmidt, Bergisch Gladbach; Harry Strang, Düsseldorf, all of Fed. Rep. of Germany

[73] Assignee: Bayer Aktiengesellschaft, Leverkusen, Fed. Rep. of Germany

[21] Appl. No.: 79,726

[22] Filed: Jul. 30, 1987

[30] Foreign Application Priority Data

Aug. 13, 1986 [DE] Fed. Rep. of Germany ....... 3627411

[51] Int. Cl.$^4$ .................... C07D 487/04; A61K 31/14
[52] U.S. Cl. ........................................ 71/92; 544/263
[58] Field of Search ............................ 544/263; 71/92

[56] References Cited

U.S. PATENT DOCUMENTS

4,312,663 1/1982 Mikhail .................... 71/90
4,740,233 4/1988 Kleschick .................... 544/263

FOREIGN PATENT DOCUMENTS

0142152 5/1985 European Pat. Off. .
0183848 6/1986 European Pat. Off. .
190375 8/1986 European Pat. Off. ............ 544/263
1620694 12/1970 Fed. Rep. of Germany .
2327133 1/1974 Fed. Rep. of Germany .
48-35456 10/1973 Japan .................... 544/263
951652 3/1964 United Kingdom .

*Primary Examiner*—Anton H. Sutto
*Assistant Examiner*—Carol L. Cseh
*Attorney, Agent, or Firm*—Sprung Horn Kramer & Woods

[57] ABSTRACT

Novel herbicides of the formula

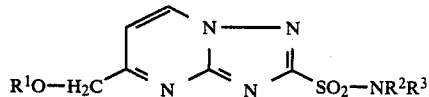

in which
R$^1$ represents alkyl,
R$^2$ represents hydrogen, alkyl, alkylcarbonyl, alkoxycarbonyl, alkylsulphonyl, alkenyl, alkinyl or optionally substituted aralkyl, and
R$^3$ represents optionally substituted aryl.

Intermediates of the formula

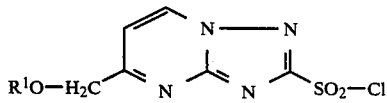

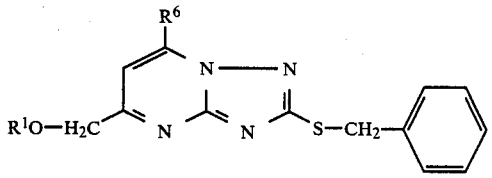

in which
R$^6$ is hydrogen, chlorine or hydroxyl,
are also new.

6 Claims, No Drawings

TRIAZOLO-PYRIMIDINE-2-SULPHONAMIDES HAVING HERBICIDAL UTILITY

The invention relates to new triazolo-pyrimidine-2-sulphonamide, a process and new intermediates for the preparation of these, and the use of these as herbicides.

It is already known that certain triazolo-pyrimidine-2-sulphonamide derivatives, such as, for example, 2,6-dimethyl-N-(2-methoxycarbonylphenyl)-1,2,4-triazolo-[1,5-a]-pyrimidine-2-sulphonamide, have herbicidal properties (cf., for example, EP-A No. 142,152). The action of this compound is good, but some weeds are not always fully covered at low application rates, and, in addition, the selectivity is not always satisfactory.

New triazolo-pyrimidine-2-sulphonamides of the formula (I),

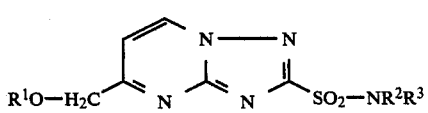

(I)

in which
R$^1$ represents alkyl,
R$^2$ represents hydrogen, alkyl, alkylcarbonyl, alkoxycarbonyl, alkylsulphonyl, alkenyl, alkinyl or optionally substituted aralkyl, and
R$^3$ represents optionally substituted aryl
have now been found.

It has furthermore been found that the new triazolo-pyrimidine-2-sulphonamides of the formula (I) are obtained when triazolo-pyrimidine-sulphonyl chlorides of the formula (II)

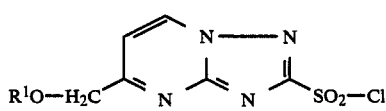

(II)

in which
R$^1$ has the abovementioned meaning,
are reacted with amines of the formula (III)

R$^3$NH$_2$     (III)

in which
R$^3$ has the abovementioned meaning,
if appropriate in the presence of acid acceptors, if appropriate in the presence of catalysts and if appropriate in the presence of diluents, and the triazolo-pyrimidine-2-sulphonamides of the formula (Ia)

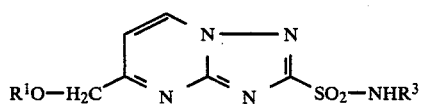

(Ia)

in which
R$^1$ and R$^3$ have the abovementioned meanings,
produced in this reaction are subsequently reacted, if appropriate, with compounds of the formula (IV)

R$^4$W     (IV)

in which

R$^4$ has the same meaning as R$^2$, but does not represent hydrogen, and
W represents a nucleophilic leaving group,
if appropriate in the presence of acid acceptors and if appropriate in the presence of diluents.

Finally, it has been found that the new triazolo-pyrimidine-2-sulphonamides of the formula (I) are distinguished by an excellent herbicidal action. Surprisingly, the triazolo-pyrimidine-2-sulphonamides according to the invention have a significantly better herbicidal activity than the compound 2,6-dimethyl-N-(2-methoxycarbonylphenyl)-1,2,4-triazolo-[1,5-a]-pyrimidine-2-sulphonamide, which is a constitutionally similar active compound of the same direction of action.

In the aliphatic substituents, the hydrocarbon chain in the definitions is in each case straight-chain or branched. Halogen in each case represents fluorine, chlorine, bromine and iodine.

Formula (I) provides a general definition of the triazolo-pyrimidine-2-sulphonamides according to the invention. Preferred compounds of the formula (I) are those in which R$^1$ represents alkyl having 1 to 6 carbon atoms,
R$^2$ represents hydrogen, alkyl, alkylcarbonyl, alkoxycarbonyl and alkylsulphonyl in each case having 1 to 6 carbon atoms in the alkyl part, alkenyl and alkinyl in each case having 3 to 8 carbon atoms, or aralkyl, having 6 to 10 carbon atoms in the aryl part and 1 to 4 carbon atoms in the alkyl part, which is optionally monosubstituted or polysubstituted in the aryl part, the substituents being identical or different and suitable aryl substituents being:
halogen, such as fluorine, chlorine, bromine or iodine, cyano, nitro, hydroxyl, C$_1$-C$_6$-alkyl, C$_1$-C$_6$-alkoxy, C$_1$-C$_6$-alkylthio, halogeno-C$_1$-C$_6$-alkyl, halogeno-C$_1$-C$_6$-alkoxy or halogeno-C$_1$-C$_6$-alkylthio, and
R$^3$ represents aryl, having 6 to 10 carbon atoms, which is optionally monosubstituted to polysubstituted, the substituents being identical or different and suitable aryl substituents being: halogen, such as fluorine, chlorine, bromine or iodine; nitro; cyano; hydroxy; C$_1$-C$_6$-alkyl; C$_1$-C$_6$-alkoxy, C$_1$-C$_6$-alkylthio; halogeno-C$_1$-C$_6$-alkyl; halogeno-C$_1$-C$_6$-alkoxy, halogeno-C$_1$-C$_6$-alkylthio; C$_1$-C$_6$-alkylcarbonyl; C$_1$-C$_6$-alkylsulphinyl; C$_1$-C$_6$-alkylsulphonyl; halogeno-C$_1$-C$_6$-alkylsulphinyl; halogeno-C$_1$-C$_6$-alkylsulphonyl; phenyl; phenoxy; phenylcarbonyl; hydroxycarbonyl, C$_1$-C$_6$-alkoxycarbonyl; C$_3$-C$_6$-alkenyloxycarbonyl; C$_1$-C$_4$-alkoxy-C$_1$-C$_6$-alkoxycarbonyl; hydroxyimino or C$_1$-C$_6$-alkoxyimino.

Particularly preferred compounds of the formula (I), are those in which
R$^1$ represents alkyl having 1 to 4 carbon atoms,
R$^2$ represents hydrogen, C$_1$-C$_4$-alkyl, C$_1$-C$_4$-alkylcarbonyl, C$_1$-C$_4$-alkoxycarbonyl, C$_1$-C$_4$-alkylsulphonyl, C$_3$-C$_6$-alkenyl, C$_3$-C$_6$-alkinyl and phenyl-C$_1$-C$_4$-alkyl which is optionally monosubstituted to trisubstituted in the phenyl part, the substituents being identical or different and suitable phenyl substituents being:
fluorine, chlorine, bromine, iodine, hydroxyl, cyano, nitro, methyl, ethyl, n-propyl, i-propyl, n-butyl, i-butyl, sec.-butyl, tert.-butyl, methoxy, ethoxy, n-propoxy, i-propoxy, n-butoxy, i-butoxy, sec.-butoxy, tert.-butoxy, methylthio, ethylthio, n-propylthio, i-propylthio, n-butylthio, i-butylthio, sec.- butylthio, tert.-butylthio, trifluoromethyl, trifluoromethoxy or trifluoromethylthio, and $R^3$ represents phenyl which is optionally monosubstituted to trisubstituted, the substituents being identical or different and suitable phenyl substituents being:

fluorine, chlorine, bromine, iodine, nitro, cyano, hydroxyl, $C_1$–$C_4$-alkyl, $C_1$–$C_4$-alkoxy, $C_1$–$C_4$-alkylthio, halogeno-$C_1$–$C_4$-alkyl, halogeno-$C_1$–$C_4$-alkoxy, halogeno-$C_1$–$C_4$-alkylthio, $C_1$–$C_4$-alkylcarbonyl, $C_1$–$C_4$-alkylsulphinyl, $C_1$–$C_4$-alkylsulphonyl, halogeno-$C_1$–$C_4$-alkylsulphinyl, halogeno-$C_1$–$C_4$-alkylsulphonyl, phenyl, phenoxy, phenylcarbonyl, hydroxycarbonyl, $C_1$–$C_4$-alkoxycarbonyl, $C_3$–$C_6$-alkenyloxycarbonyl, $C_1$–$C_2$-alkoxy-$C_1$–$C_4$-alkoxycarbonyl, hydroxyimino or $C_1$–$C_4$-alkoxyimino.

Very particularly preferred compounds of the formula (I) are those in which $R^1$ represents methyl, ethyl, n-propyl, i-propyl, n-butyl, i-butyl or sec.-butyl, $R^2$ represents hydrogen, methyl, ethy, methylcarbonyl, ethylcarbonyl, methoxycarbonyl, ethoxycarbonyl, methylsulphonyl, ethylsulphonyl, 2-propen-1-yl, 2-propin-2-yl and benzyl which is optionally monosubstituted to trisubstituted in the phenyl part, the substituents being identical or different and suitable phenyl substituents being:

fluorine, chlorine, bromine, iodine, nitro, hydroxyl, methyl, methoxy, methylthio, trifluoromethyl, trifluoromethoxy or trifluoromethylthio, and $R^3$ represents phenyl which is optionally monosubstituted to trisubstituted, the substituents being identical or different and suitable phenyl substituents being:

fluorine, chlorine, bromine, iodine, nitro, hydroxyl, methyl, methoxy, methylthio, trifluoromethyl, trifluoromethoxy, trifluoromethylthio, methylcarbonyl, ethylcarbonyl, methylsulphinyl, methylsulphonyl, trifluoromethylsulphinyl, trifluoromethylsulphonyl, phenyl, phenoxy, phenylcarbonyl, hydroxycarbonyl, methoxycarbonyl, ethoxycarbonyl, 2-propen-1-yloxycarbonyl, methoxy-methoxycarbonyl, ethoxy-methoxycarbonyl, methoxy-ethoxycarbonyl, ethoxy-ethoxycarbonyl, hydroxyimino, methoxyimino, ethoxyimino or n-propoxyimino.

If 5-methoxymethyl-1,2,4-triazolo-[1,5-a]-pyrimidine-2-sulphonyl chloride and 2-chloro-6-methylaniline are used as starting materials, the course of the process according to the invention may be represented by the following equation:

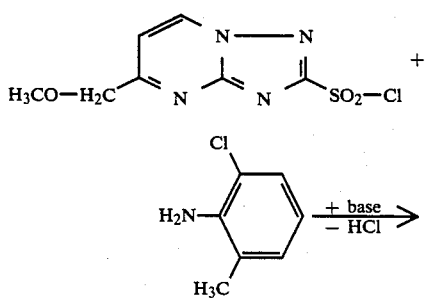

If 5-methoxymethyl-1,2,4-triazolo[1,5-a]-pyrimidine-2-sulphonyl chloride, 2-chloro-6-methylaniline and methyl iodide are used as starting materials, the course of the process according to the invention may be represented by the following equation:

Formula (II) provides a general definition of the triazolo-pyrimidine-sulphonyl chloride to be used as starting materials in the process according to the invention. In this formula (II), $R^1$ preferably represents those radicals which have already been mentioned in connection with the description of the substances of the formula (I) according to the invention as being preferred for these substituents.

The following may be mentioned as examples of triazolo-pyrimidine-sulphonyl chlorides of the formula (II):

5-methoxymethyl-, 5-ethoxymethyl-, 5-n-propoxymethyl-, 5-i-propoxymethyl-, 5-n-butoxymethyl-, 5-i-butoxymethyl- and 5-sec.-butoxymethyl-1,2,4-triazolo-[1,5-a]-pyrimidinesulphonyl chloride.

The compounds of the formula (II) are new and are part of the present invention. However, they can be prepared in a simple fashion by known methods.

Thus, the new compounds of the formula (II)

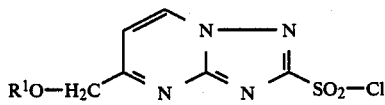
(II)

in which
R¹ represents alkyl,
are obtained when benzyl sulphides of the formula (V)

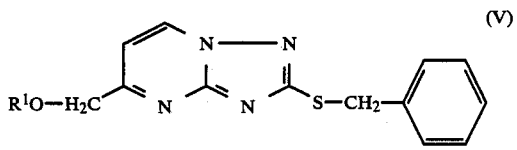
(V)

in which
R¹ has the abovementioned meaning,
are reacted with a chlorinating agent, such as, for example, elemental chlorine or sodium hypochlorite, in the presence of aqueous acids, such as, for example, aqueous hydrochloric acid or acetic acid, and, if appropriate, in the presence of water-insoluble organic diluents, such as, for example, methyl chloride or chloroform, at temperatures between −20° C. and +25° C.

The benzyl sulphides of the formula (V) are new. The compounds of the formula (V)

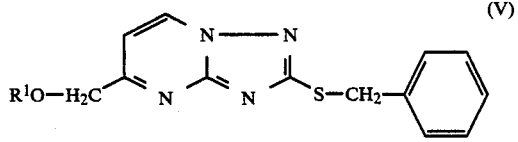
(V)

in which
R¹ represents alkyl,
are obtained when compounds of the formula (VI)

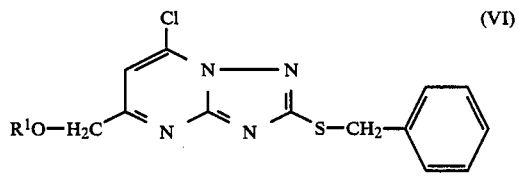
(VI)

in which
R¹ has the abovementioned meaning,
are reacted in the presence of reducing agents, such as, for example, zinc duct and copper sulphate, in the presence of acids, such as, for example, glacial acetic acid, and in the presence of diluents, such as, for example, methanol and tetrahydrofuran, at temperatures between 0° C. and 30° C.

The compounds of the formula (VI) are new. The compounds of the formula (VI)

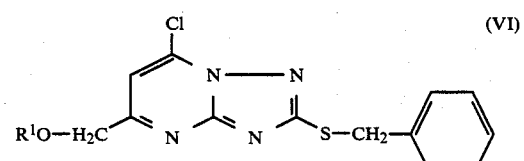
(VI)

in which
R¹ represents alkyl,
are obtained when hydroxyl derivatives of the formula (VII)

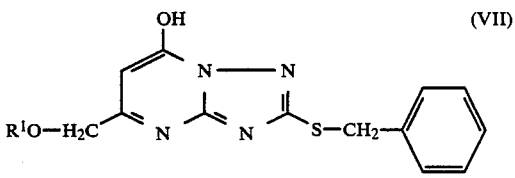
(VII)

in which
R¹ has the abovementioned meaning,
are reacted with phosphorus oxychloride, if appropriate in the presence of diluents, such as, for example, acetonitrile, at temperatures from 60° C. to 120° C.

The hydroxyl derivatives of the formula (VII) are new. The compounds of the formula (VII)

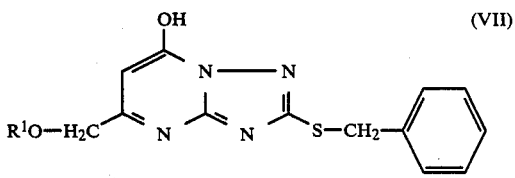
(VII)

in which
R¹ represents alkyl,
are obtained when 5-amino-3-benzylthio-1,2,4-triazole of the formula (VIII)

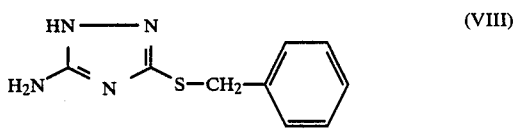
(VIII)

is reacted with alkoxyacetoacetates of the formula (IX)

(IX)

in which
R¹ has the abovementioned meanings, and
R⁵ represents C₁-C₄-alkyl,
in the presence of acids, such as, for example, glacial acetic acid, at temperatures from 80° C. to 140° C.

The compounds of the formulae (VIII) and (IX) are known (cf., for example, J. Het. Chem. 12, 1887 (1975) and DE-OS (German Published Specification) No. 2,244,012).

The compounds of the formulae (V), (VI) and (VII) can be summarized in a common formula (X):

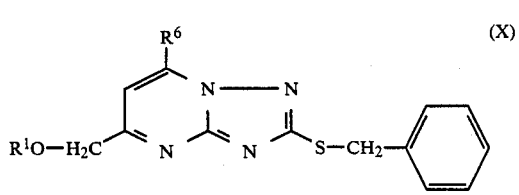
(X)

in which $R^1$ represents alkyl, preferably $C_1$–$C_6$-alkyl, in particular $C_1$–$C_4$-alkyl, and $R^6$ represents hydrogen, chlorine or hydroxyl.

The following may be mentioned as examples of the new compounds of the formulae (V), (VI) and (VII):

TABLE 1

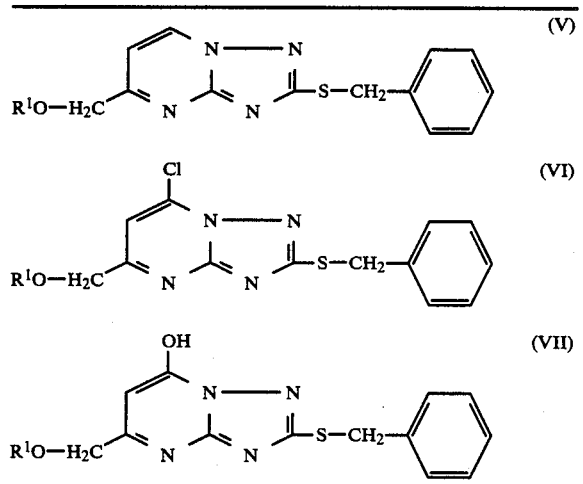

(V)

(VI)

(VII)

TABLE 1-continued

| $R^1$ | $R^1$ |
|---|---|
| $CH_3$ | n-$C_4H_9$ |
| $C_2H_5$ | i-$C_4H_9$ |
| n-$C_3H_7$ | sec.-$C_4H_9$ |
| i-$C_3H_7$ | |

Formula (III) provides a general definition of the amines additionally to be used as starting materials in the process according to the invention. In this formula (III), $R^3$ preferably represents those radicals which have already been mentioned in connection with the description of the substances of the formula (I) according to the invention as being preferred for these substituents.

The amines of the formula (III) are generally known compounds of organic chemistry.

The following may be mentioned as examples of the amines of the formula (III):

TABLE 2

$R_3NH_2$

| $R^3$ | $R^3$ |
|---|---|
| 2-Cl, 6-CH$_3$-phenyl | 2,6-Cl$_2$-phenyl |
| 2-Cl, 6-Br-phenyl | 2-Cl, 6-I-phenyl |
| 2,6-F$_2$-phenyl | 2-Cl, 6-F-phenyl |
| 2-CF$_3$-phenyl | 2-CH$_3$, 3-Cl, 6-Cl-phenyl |
| 2-CH$_3$, 5-CO$_2$CH$_3$-phenyl | 2-CH$_3$, 5-CO$_2$C$_2$H$_5$-phenyl |

TABLE 2-continued

R₃NH₂

R³ — (o-tolyl with CO₂—CH₂—CH=CH₂)

R³ — (o-tolyl with CO₂—CH₂—CH₂—O—CH₃)

(o-tolyl with CO₂—CH₂—CH₂—O—C₂H₅)

(phenyl with NO₂ and CH₃)

(phenyl with NO₂, H₃C and CH₃)

Formula (IV) provides a general definition of the compounds furthermore to be used as starting materials in the process according to the invention. In this formula (IV), $R^4$ preferably represents those radicals which have already been mentioned in connection with the description of the substances of the formula (I) according to the invention as being preferred for the substituents $R^2$, but where $R^4$ does not represent hydrogen. In formula (IV), W represents a nucleophilic leaving group, preferably chloride, bromide, iodide, —O—SO₂—OCH₃, —O—SO₂CH₃ and

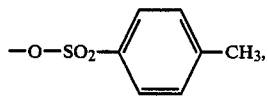

in particular chloride.

The following may be mentioned as examples of compounds of the formula (IV):

TABLE 4

$R^4W$ (IV)

| $R^4$ | $R^4$ | $R^4$ |
|---|---|---|
| —CH₃ | —C₂H₅ | —C₃H₇—n |
| —C₃H₇—i | —C₄H₉—n | —C₄H₉—i |
| —CO—CH₃ | —COC₂H₅ | —COOCH₃ |
| —COOC₂H₅ | —SO₂CH₃ | —SO₂C₂H₅ |
| —COOC₃H₇—n | —COOC₄H₉—n | —COC₃H₇—n |
| —COC₄H₉—n | —CH₂—CH=CH₂ | —CH₂—C≡CH |

—CH₂—(phenyl)

W = chloride,

The process according to the invention for the preparation of the new triazolo-pyrimidine-2-sulphonamides of the formula (Ia) is preferably carried out using diluents. Suitable diluents in this process are virtually all inert organic solvents. These preferably include aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl and dibutyl ether, glycol dimethyl ether and diglycol dimethyl ether, tetrahydrofuran and dioxane, ketones, such as acetone, methyl ethyl, methyl isopropyl and methyl isobutyl ketone, esters, such as methyl acetate and ethyl acetate, nitriles, such as, for example, acetonitrile and propionitrile, amides, such as, for example, dimethylformamide, dimethylacetamide and N-methyl-pyrrolidone, and also dimethyl sulphoxide, tetramethylene sulphone, hexamethylphosphoric triamide and pyridine.

The process, according to the invention, for the preparation of the compounds of the formula (Ia) is preferably carried out in the presence of acid acceptors. Acid acceptors which can be employed in the process according to the invention are all acid-binding agents which can usually be used for such reactions. Alkali metal hydrides, such as, for example, sodium hydride and potassium hydride, alkali metal alkyl compounds, such as, for example, butyllithium, alkali metal hydroxides, such as, for example, sodium hydroxide and potassium hydroxide, alkaline-earth metal hydroxides, such as, for example, calcium hydroxide, alkali metal carbonates and alcoholates, such as sodium carbonate and potassium carbonate, sodium methylate and ethylate and potassium methylate and ethylate, furthermore aliphatic, aromatic or heterocyclic amines, for example triethylamine, trimethylamine, dimethylanilin, dimethylbenzylamine, pyridine, dimethylaminopyridine, N-methylmorpholine, 1,5-diazabicyclo-[4,3,0]-non-5-ene (DBN), 1,8-diazabicyclo-[5,4,0]-undec-7-ene (DBU) and 1,4-diazabicyclo-[2,2,2]-octane (DABCO).

Catalysts which can be used in the process according to the invention are basic catalysts. The following are preferably suitable: aliphatic, aromatic or heterocyclic amines, such as triethylamine, trimethylamine, dimethylaminopyridine, dimethylaniline and N-methylmorpholine.

The reaction temperatures can be varied within a relatively wide range in the process according to the invention. In general, the process is carried out at temperatures between 0° C. and 160° C., preferably at temperatures between 0° C. and 140° C.

The process according to the invention is generally carried out at atmospheric pressure. However, it is also possible to carry out the process under increased or reduced pressure.

The starting materials of the formula (II) and (III) required in each case for carrying out the process according to the invention are generally employed in approximately equimolar amounts. If the compound of the formula (III) has a low reactivity, it is more advantageous to first react the amine of the formula (III) with a strong base, such as, for example, sodium hydride or butyllithium, at temperatures between −80° C. and 0° C. and to further react the metal derivative thus obtained with the compound of the formula (II). In this case, 2 to 3 moles of amine are employed per mole of the compound of the formula (II). The reactions are generally carried out in a suitable diluent in the presence of an acid acceptor and if appropriate in the presence of a catalyst, and the reaction mixture is stirred for several hours at the temperature required in each case. In the process according to the invention, work-up is in each case carried out by conventional methods.

If it is intended to prepare a compound of the formula (I) in which $R^2$ does not represent hydrogen, a procedure is followed in which a compound of the formula (Ia) prepared by the process according to the invention is reacted with a compound of the formula (IV). This reaction is preferably carried out in the presence of suitable diluents. The following are suitable as diluents for this: ethers, such as diethyl and dibutyl ether, glycol dimethyl ether and di-glycol dimethyl ether, tetrahydrofuran and dioxane, ketones, such as acetone, methyl ethyl, methyl isopropyl and methyl isobutyl ketone, nitriles, such as, for example, acetonitrile and propionitrile, amides, such as, for example, dimethylformamide, and also dimethyl sulphoxides and alcohols, such as, for example, methanol, ethanol, isopropanol and tert.-butanol.

The following acid acceptors are preferably suitable for these reactions: alkali metal hydroxides, such as, for example, sodium hydroxide and potassium hydroxide, alkaline-earth metal hydroxides, such as, for example, calcium hydroxide, alkali metal carbonates and alcoholates, such as sodium carbonate and potassium carbonate, sodium methylate and ethylate and potassium methylate and ethylate and potassium tert.-butylate, furthermore aliphatic, aromatic or heterocyclic amines, for example triethylamine, trimethylamine, dimethylaniline, dimethylbenzylamine, pyridine and 4-dimethylaminopyridine.

The reaction for the preparation of the compounds of the formula (I) from compounds of the formula (Ia) are generally carried out at temperatures between 0° C. and 120° C., preferably at temperatures between 20° C. and 100° C.

The starting materials of the formulae (Ia) and (IV) are generally employed in approximately equimolar amounts for carrying out the reaction. However, it is alo possible to use one of the two components employed in each case in a relatively large excess. The reactions are generally carried out in a suitable diluent in the presence of an acid acceptor, and the reaction mixture is stirred for several hours at the temperature required in each case. Work-up is carried out by conventional methods.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The compounds of the formula (I) according to the invention are particularly suitable for selective combating of mono- and dicotyledon weeds, in particular in the post-emergence method in crops such as, for example, soya.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silicic acid, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain betwen 0.1 and 95 percent by weight of active compound, preferably between 0.5 and 90%.

The active compounds according to the invention, as such or in the form of their formulations, can also be used, for combating weeds, as mixtures with known herbicides, ready-to-use formulations or tank mixes being possible.

Known herbicides, such as, for example, ethyl 2-{[(4-chloro-6-methoxy-2-pyrimidyl)-aminocarbonyl]-aminosulphonyl}-benzoate, 4-amino-6-(1,1-dimethylethyl)-3-methylthio-1,2,4-triazin-5(4H)-one, 4-amino-3-methyl-6-phenyl-1,2,4-triazin-5(4H)-one, 5-(2-chloro-4-trifluoromethyl-phenoxy)-2-nitrobenzoic acid, 5-(2-chloro-4-trifluoromethyl-phenoxy)-N-methylsulphonyl-2-nitrobenzamide, 2-ethoxy-1-methyl-2-oxo-ethyl 5-(2-chloro-4-trifluoromethyl-phenoxy)-2-nitro-benzoate, 2-{4-[(3-chloro-5-trifluoromethyl-2-pyridinyl)oxy]-phenoxy}-propionic acid, the R enantiomer of the (trimethylsilyl)-methyl ester of 2-{4-[(3,5-dichloro-2-pyridinyl)oxy]-pheonxy}-propionic acid, 2,4-dichloro-phenoxyacetic acid, 2-(2,4-dichlorophonoxy)-propionic acid, 4-chloro-2-methyl-phenoxy-acetic acid, 2-(4-chloro-2-methyl-phenoxy)-propionic acid, 2-[5-methyl-5-(1-methylethyl)-4-oxo-2-imidazolin-2-yl]-3-pyridinecarboxylic acid, 2-(1-ethoxyamino-butylidene)-5-(2-ethylthiopropyl)-1,3-cyclohexanedione, 2-[1-(ethoxyimino)-butyl]-3-hydroxy-5-(tetrahydro-2H-thiopyran-3-yl)-2-cyclohexen-1-one, the sodium salt of 2-(1-alloxyaminobutylidene)-4-methoxycarbonyl-5-5-dimethylcyclohexane-1,3-dione and 3-isopropyl-2,1,3-benzothiadiazin-4-one 2,2-dioxide can be used for the mixtures. Surprisingly, some mixtures also have a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing and scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

The preparation and use of the active compounds according to the invention can be seen from the following examples.

PREPARATION EXAMPLES

EXAMPLE 1

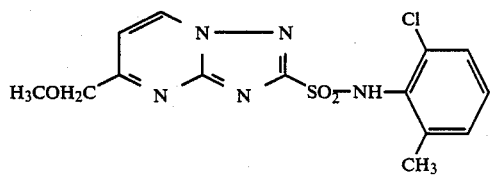

1.0 g (0.0038 mol) of 5-methoxymethyl-1,2,4-triazolo-[1,5-a]-pyrimidine-2-sulphonyl chloride are added to a solution of 0.3 g (0.0038 mol) of pyridine, 0.05 g (0.00041 mol) of 4-dimethylaminopyridine and 0.54 g (0.0038 mol) of 2-chloro-6-methylaniline in 20 ml of dichloromethane, and the mixture is stirred for 24 hours at 20° C. The mixture is substantially concentrated, and the residue is purified chromatographically over silica gel.

0.8 g (57% of theory) of 5-methoxymethyl-N-(2-chloro-6-methyl-phenyl)-1,2,4-triazolo-[1,5-a]-pyrimidine-2-sulphonamide is obtained as a colorless solid of melting point 196° C.

The following compounds of the formula (I) can be prepared analogously to Example 1 and to the general instructions for the preparation:

TABLE 4
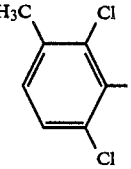
(I)
| Example No. | R¹ | R² | R³ | Physical data |
|---|---|---|---|---|
| 2 | $CH_3$ | H | 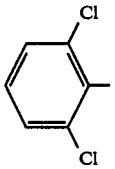 | m.p. 210° C. |
| 3 | $CH_3$ | H | 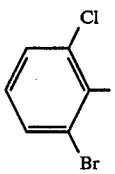 | m.p. 209° C. (decomp.) |
| 4 | $CH_3$ | H | 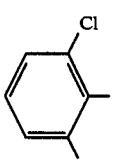 | |
| 5 | $CH_3$ | H | 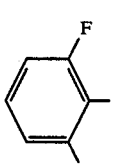 | |
| 6 | $CH_3$ | H | 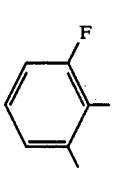 | m.p. 188° C. |
| 7 | $CH_3$ | H | 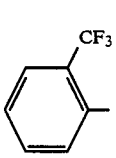 | |
| 8 | $CH_3$ | H | 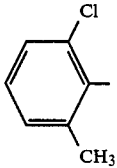 | |
| 9 | $C_2H_5$ | H |  | |

TABLE 4-continued $$R^1O-H_2C\text{-(structure)-}SO_2-NR^2R^3 \quad (I)$$

| Example No. | R¹ | R² | R³ | Physical data |
|---|---|---|---|---|
| 10 | C₂H₅ | H | 2,6-dichlorophenyl | |
| 11 | C₂H₅ | H | 2,4-dichloro-6-methylphenyl (H₃C, Cl, Cl) | |
| 12 | CH₃ | CH₃ | 2,6-dimethyl... (Cl, CH₃) | |
| 13 | CH₃ | —CH₂—C₆H₅ | 2-Cl-6-CH₃-phenyl | |
| 14 | CH₃ | —CH₂—CH=CH₂ | 2-Cl-6-CH₃-phenyl | |
| 15 | CH₃ | —CH₂—C≡CH | 2-Cl-6-CH₃-phenyl | |
| 16 | CH₃ | —COCH₃ | 2-Cl-6-CH₃-phenyl | |
| 17 | CH₃ | —COOCH₃ | 2-Cl-6-CH₃-phenyl | |

TABLE 4-continued (I)

R¹O—H₂C... N...N... SO₂—NR²R³

| Example No. | R¹ | R² | R³ | Physical data |
|---|---|---|---|---|
| 18 | CH₃ | —SO₂CH₃ | 2-Cl, 3-CH₃ phenyl | |
| 19 | CH(CH₃)₂ | H | 2-Cl, 3-CH₃ phenyl | |
| 20 | CH(CH₃)₂ | H | 2-CH₃, 4-COOCH₃ phenyl | |
| 21 | CH(CH₃)₂ | H | 2-Br, 3-CH₃ phenyl | |
| 22 | CH₃ | H | 2-Br, 3-CH₃ phenyl | |
| 23 | CH₃ | H | 2-CH₃, 4-COOCH₃ phenyl | m.p. 161° C. |

STARTING MATERIALS OF THE FORMULA (II)

EXAMPLE (II-1)

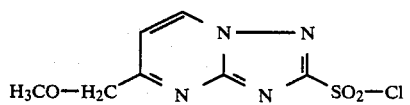

8.6 g (0.030 mol) of 2-benzylthio-5-methoxymethyl-1,2,4-triazolo-[1,5-a]-pyrimidine are suspended in 50 ml of glacial acetic acid/water 1:1, and chlorine gas is passed through the suspension at a temperature of −5° C. for 30 minutes. The product precipitated out is filtered off under suction, washed with glacial acetic acid and dried.

5.3 g (67%) of 5-methoxymethyl-1,2,4-triazolo-[1,5-a]-pyrimidine-2-sulphonyl chloride are obtained as a beige powder of melting point 125° C.

The following compounds of the formula (II) can be obtained analogously to Example (II-1):

TABLE 5

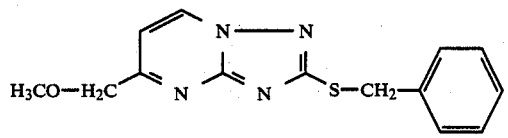

| Example No. | R¹ | Physical data |
|---|---|---|
| II-2 | $C_2H_5$ | |
| II-3 | $C_3H_7-i$ | |

STARTING MATERIALS OF THE FORMULA (V)

EXAMPLE (V-1)

A zinc-copper pair is prepared corresponding to J. Org. Chem. 31, 626 (1966) by stirring 10 g of copper sulphate with 150 g of zinc dust in 200 ml of water for 2 hours. The product is filtered off under suction, washed with acetone and dried overnight at 100° C. in vacuo.

2.32 g (0.039 mol) of glacial acetic acid and subsequently 3.8 g of the abovementioned zinc-copper pair are added to 6.2 g (0.019 mol) of 2-benzylthio-7-chloro-5-methoxymethyl-1,2,4-triazolo-[1,5-a]-pyrimidine, 10 ml of methanol and 60 ml of tetrahydrofuran at 20° C. with external cooling, and the mixture is stirred for 2 hours and poured through kieselguhr. The filtrate is concentrated, and the residue is purified chromatographically over silica gel.

5.3 g (96% of theory) of 2-benzylthio-5-methoxymethyl-1,2,4-triazolo-[1,5-a]-pyrimidine are obtained as a yellow solid of melting point 92° C.

The following compounds of the formula (V) can be obtained analogously to Example (V-1):

TABLE 6

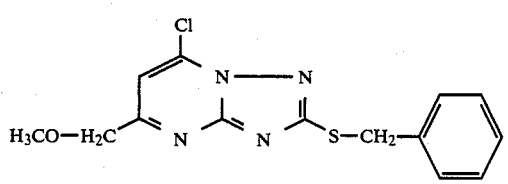

| Example No. | R¹ | Physical data |
|---|---|---|
| V-2 | $C_2H_5$ | |
| V-3 | $C_3H_7-i$ | |

STARTING MATERIALS OF THE FORMULA (VI)

EXAMPLE (VI-1)

A solution of 22.8 g (0.075 mol) of 2-benzylthio-5-methoxymethyl-7-hydroxy-1,2,4-triazolo-[1,5-a]-pyrimidine and 35 g (0.228 mol) of phosphorus oxychloride in 200 ml of acetonitrile is refluxed for 4 hours. After cooling, the solvent and excess phosphorus oxychloride are removed. The residue is taken up in methylene chloride and water, and the organic phase is dried over magnesium sulphate and concentrated in vacuo. The residue is purified through a silica gel column using ether as eluant.

19.0 g (78.5% of theory) of 2-benzylthio-7-chloro-5-methoxymethyl-1,2,4-triazolo-[1,5-a]-pyrimidine are obtained as a colorless powder of melting point 79° C.

The following compounds of the formula (VI) can be obtained analogously to Example (VI-I):

TABLE 7

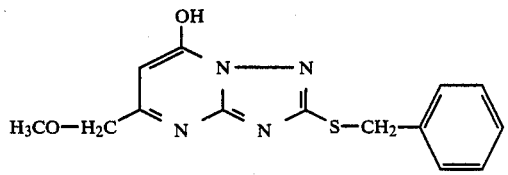

| Example No. | R¹ | Physical data |
|---|---|---|
| VI-2 | $C_2H_5$ | |
| VI-3 | $C_3H_7-i$ | |

STARTING MATERIALS OF THE FORMULA (VII)

EXAMPLE (VII-1)

A mixture of 20 g (0.97 mol) of 3-amino-5-benzylthio-1,2,4-triazolo and 14.2 g (0.097 mol) of methyl 4-methoxyacetoacetate in 200 ml of glacial acetic acid is refluxed for 3 hours. After cooling, the precipitated-out product is filtered off under suction and stirred with ice-cold ethanol.

24 g (82% of theory) of 2-benzylthio-7-hydroxy-5-methoxymethyl-1,2,4-triazolo-[1,5-a]-pyrimidine of melting point 213° C. are obtained.

The following compounds of the formula (VII) can be obtained analogously to Example (VII-1):

TABLE 8

| Example No. | R¹ | Physical data |
|---|---|---|
| VII-2 | $C_2H_5$ | |
| VII-3 | $C_3H_7-i$ | |

USE EXAMPLES

The compound specified below is employed as comparison compound in the following use example:

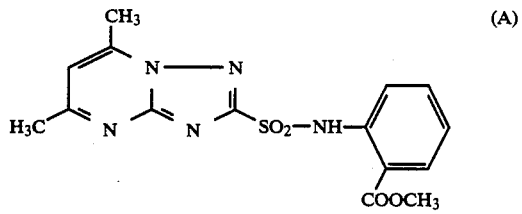

known from EP-A No. 142,152

EXAMPLE A

POST-EMERGENCE TEST

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way so as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0%=no action (like untreated control)
100%=total destruction.

In this test, the compound according to preparation Example (1), for example, exhibits a clearly superior activity against weeds such as, for example, Amaranthus, Datura and Ipomoea, and compatibility, for example in soybeans, compared to comparison example (A).

It will be understood that the specification and examples are illustrative but not limitative of the present invention and the other embodiments within the spirit and scope of the invention will suggest themselves to those skilled in the art.

We claim:

1. A triazolo-pyrimidine-2-sulphonamide of the formula

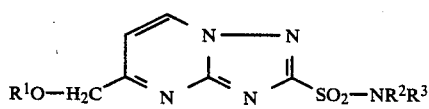

in which
 $R^1$ represents alkyl having 1 to 6 carbon atoms,
 $R^2$ represents hydrogen, alkyl, alkylcarbonyl, alkoxycarbonyl and alkylsulphonyl in each case having 1 to 6 carbon atoms in the alkyl part, alkenyl and alkinyl in each case having 3 to 8 carbon atoms, or aralkyl, having 6 to 10 carbon atoms in the aryl part and 1 to 4 carbon atoms in the alkyl part, which is optionally monosubstituted or polysubstituted in the aryl part, the substituents being identical or different and being fluorine, chlorine, bromine, iodine, cyano, nitro, hydroxyl, $C_1$-$C_6$-alkyl, $C_1$-$C_6$-alkoxy, $C_1$-$C_6$-alkylthio, halogeno-$C_1$-$C_6$-alkyl, halogeno-$C_1$-$C_6$-alkoxy or halogeno-$C_1$-$C_6$-alkylthio, and
 $R^3$ represents aryl, having 6 to 10 carbon atoms, which is optionally monosubstituted to polysubstituted, the substituents being identical or different and being
fluorine, chlorine, bromine or iodine; nitro; cyano; hydroxyl; $C_1$-$C_6$-alkyl; $C_1$-$C_6$-alkoxy, $C_1$-$C_6$-alkylthio; halogeno-$C_1$-$C_6$-alkyl; halogeno-$C_1$-$C_6$-alkoxy, halogeno-$C_1$-$C_6$-alkylthio; $C_1$-$C_6$-alkylcarbonyl; $C_1$-$C_6$-alkylsulphinyl; $C_1$-$C_6$-alkylsulphonyl; halogeno-$C_1$-$C_6$-alkylsulphinyl; halogeno-$C_1$-$C_6$-alkylsulphonyl; phenyl; phenoxy; phenylcarbonyl; hydroxycarbonyl, $C_1$-$C_6$-alkoxycarbonyl; $C_3$-$C_6$-alkenyloxycarbonyl; $C_1$-$C_4$-alkoxy-$C_1$-$C_6$-alkoxy-carbonyl; hydroxyimino or $C_1$-$C_6$-alkoxyimino.

2. A triazolo-pyrimidine-2-sulphonamide according to claim 1, in which
 $R^1$ represents alkyl having 1 to 4 carbon atoms,
 $R_2$ represents hydrogen, $C_1$-$C_4$-alkyl, $C_1$-$C_4$-alkylcarbonyl, $C_1$-$C_4$-alkoxycarbonyl, $C_1$-$C_4$-alkylsulphonyl, $C_3$-$C_6$-alkenyl, $C_3$-$C_6$-alkinyl or phenyl-$C_1$-$C_4$-alkyl which is optionally monosubstituted to trisubstituted in the phenyl part, the substituents being identical or different and being
fluorine, chlorine, bromine, iodine, hydroxyl, cyano, nitro, methyl, ethyl, n-propyl, i-propyl, n-butyl, i-butyl, sec.-butyl, tert.-butyl, methoxy, ethoxy, n-propoxy, i-propoxy, n-butoxy, i-butoxy, sec.-butoxy, tert.-butoxy, methylthio, ethylthio, n-propylthio, i-propylthio, n-butylthio, i-butylthio, sec.-butylthio, tert.-butylthio, trifluoromethyl, trifluoromethoxy or trifluoromethylthio, and
 $R^3$ represents phenyl which is optionally monosubstituted to trisubstituted, the substituents being identical or different and being
fluorine, chlorine, bromine, iodine, nitro, cyano, hydroxyl, $C_1$-$C_4$-alkyl, $C_1$-$C_4$-alkoxy, $C_1$-$C_4$-alkylthio, halogeno-$C_1$-$C_4$-alkyl, halogeno-$C_1$-$C_4$-alkoxy, halogeno-$C_1$-$C_4$-alkylthio, $C_1$-$C_4$-alkylcarbonyl, $C_1$-$C_4$-alkylsulphinyl, $C_1$-$C_4$-alkylsulphonyl, halogeno-$C_1$-$C_4$-alkylsulphinyl, halogeno-$C_1$-$C_4$-alkylsulphonyl, phenyl, phenoxy, phenylcarbonyl, hydroxycarbonyl, $C_1$-$C_4$-alkoxycarbonyl, $C_3$-$C_6$-alkenyloxycarbonyl, $C_1$-$C_2$-alkoxy-$C_1$-$C_4$-alkoxycarbonyl, hydroxyimino or $C_1$-$C_4$-alkoxyimino.

3. A compound according to claim 1, wherein such compound is 5-methoxymethyl-N-(2-chloro-6-methyl-phenyl)-1,2,4-triazolo-[1,5-a]-pyrimidine-2-sulphonamide of the formula

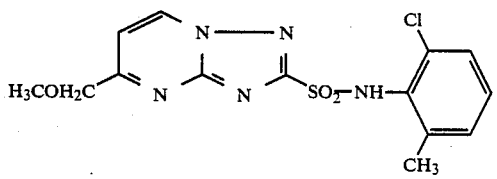

4. A herbicidal composition comprising a herbicidally effective amount of a compound according to claim 1 and diluent.

5. A method of combating unwanted vegetation which comprises applying to such vegetation or to a locus from which it is desired to exclude such vegetation a herbicidally effective amount of a compound according to claim 1.

6. The method according to claim 5, wherein such compound is 5-methoxymethyl-N-(2-chloro-6-methylphenyl)-1,2,4-triazolo-[1,5-a]-pyrimidine-2-sulphonamide.

* * * * *